United States Patent
Scheidt et al.

(10) Patent No.: US 9,090,634 B2
(45) Date of Patent: Jul. 28, 2015

(54) AZOLIUM METAL-ORGANIC FRAMEWORKS

(71) Applicants: Karl A. Scheidt, Evanston, IL (US);
John M. Roberts, Evanston, IL (US);
Joseph T. Hupp, Northfield, IL (US);
Omar K. Farha, Morton Grove, IL (US)

(72) Inventors: Karl A. Scheidt, Evanston, IL (US);
John M. Roberts, Evanston, IL (US);
Joseph T. Hupp, Northfield, IL (US);
Omar K. Farha, Morton Grove, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 13/889,988

(22) Filed: May 8, 2013

(65) Prior Publication Data
US 2013/0317228 A1    Nov. 28, 2013

Related U.S. Application Data (60) Provisional application No. 61/644,246, filed on May 8, 2012.

(51) Int. Cl.
*C07D 233/54* (2006.01)
*C07F 3/06* (2006.01)
*C07F 1/08* (2006.01)
*C07F 3/00* (2006.01)

(52) U.S. Cl.
CPC ... *C07F 3/06* (2013.01); *C07F 1/08* (2013.01); *C07F 3/003* (2013.01)

(58) Field of Classification Search
CPC .............................. C07D 233/54; C07F 3/06
See application file for complete search history.

(56) References Cited

PUBLICATIONS

Roberts, John M. Two Azolium Rings Are Better Than One: A strategy for Controlling Catenation and Morphology in Zn and Cu Metal—Organic Frameworks. Crystal Growth and Design. 2011, 11, 4747-4750.*
Ferey, G., "Hybrid porous solids: past, present, future", Chem. Soc. Rev. 2008, 37, 191-214.
Murray, L. et al., "Hyrdrogen storage in metal-organic frameworks", Chem. Soc. Rev. 2009, 38, 1294-1314.
Farha, O. K. et al., "De novo synthesis of a metal-organic framework material featuring ultrahigh surface area and gas storage capacities", Nat. Chem. 2010, 2, 944-948.
Furukawa, H. et al., "Ultrahigh Porosity in Metal-Organic Frameworks", Science 2010, 329, 424-428.
Li, J. R. et al., "Selective gas adsorption and separation in metal-organic frameworks", Chem. Soc. Rev. 2009, 38, 1477-1504.
Lee, J. et al., "Metal-organic framework materials as catalysts", Chem. Soc. Rev. 2009, 38, 1450-1459.
Farha, O. K. et al., "Separating Solids: Purification of Metal-Organic Framework Materials", J. Am. Chem. Soc. 2008, 130, 8598-8599.
Shekhah, O. et al., "Step-by-Step Route for the Synthesis of Metal-Organic Frameworks", J. Am. Chem. Soc. 2007, 129, 15118-15119.
Shekhah, O. et al., "Controlling interpenetration in metal-organic frameworks by liquid-phase epitaxy", Nat. Mater. 2009, 8, 481-484.
Ma, S. Q. et al., "Framework-Catenation Isomerism in Metal-Organic Frameworks and Its Impact on Hydrogen Uptake", J. Am. Chem. Soc. 2007, 129, 1858-1859.
Ma, L. Q. et al., "Chirality-Controlled and Solvent-Templated Catenation Isomerism in Metal-Organic Frameworks", J. Am. Chem. Soc. 2008, 130, 13834-13835.
Wang, Q. et al., "Guest Inclusion and Interpenetration Tuning of Cd(II)Mn(II) Coordination Grid Networks Assembled from a Rigid Linear Diimidazole Schiff Base Ligand", Inorg. Chem. 2009, 48, 287-295.
Song, F. J. et al., "Isoreticular Chiral Metal-Organic Frameworks for Asymmetric Alkene Epoxidation: Tuning Catalytic Activity by Controlling Framework Catenation and Varying Open Channel Sizes", J. Am. Chem. Soc. 2010, 132, 15390-15398.
He, H.Y. et al., "Control over Interpenetration in Lanthanide-Organic Frameworks: Synthetic Strategy and Gas-Adsorption Properties", Inorg. Chem. 2010, 49, 7605-7607.
Eddaoudi, M. et al., "Systematic Design of Pore-Size and Functionality in Isoreticular MOFs and Their Application in Methane Storage", Science 2002, 295, 469-472.
Zhang, J. J. et al., "Temperature and Concentration Control over Interpenetration in a Metal-Organic Material", J. Am. Chem. Soc. 2009, 131, 17040-17041.
Farha, O. K. et al., "An Example of Node-Based Postassembly Elaboration of a Hydrogen-Sorbing, Metal-Organic Framework Material", Inorg. Chem. 2008, 47, 10223-10225.
Farha, O. K. et al., "Control over Catenation in Metal-Organic Frameworks via Rational Design of the Organic Building Block", J. Am. Chem. Soc. 2010, 132, 950-952.
Lee, J. Y. et al., "Synthesis and Gas Sorption Properties of a Metal-Azolium Framework (MAF) Material", Inorg. Chem. 2009, 48, 9971-9973.
Fei, Z. F. et al., "A Nearly Planar Water Sheet Sandwiched between Strontium-Imidazolium Carboxylate Coordination Polymers", Inorg. Chem. 2005, 44, 5200-5202.
Fei, Z. F. et al., "Metal-Organic Frameworks Derived from Imidazolium Dicarboxylates and Group I and II Salts", Inorg. Chem. 2006, 45, 6331-6337.
Chun, J. et al., "Concomitant Formation of N-Heterocyclic Carbene-Copper Complexes within a Supramolecular Network in the Self-Assembly of Imidazolium Dicarboxylate with Metal Ions", Inorg. Chem. 2009, 48, 6353-6355.
Han, L. J. et al., "A Strategy for Synthesis of Ionic Metal-Organic Frameworks", Inorg. Chem. 2009, 48, 786-788.
Chun, J. et al., "Cu2O: A Versatile Reagent for Base-Free Direct Synthesis of NHC-Copper Complexes and Decoration of 3D-MOF with Coordinatively Unsaturated NHC-Copper Species Organometallics", 2010, 29, 1518-1521.
Oisaki, K. et al., "A Metal-Organic Framework with Covalently Bound Organometallic Complexes", J. Am. Chem. Soc. 2010, 132, 9262-9264.

(Continued)

*Primary Examiner* — Samantha Shterengarts
(74) *Attorney, Agent, or Firm* — Reinhart Boerner Van Deuren s.c.

(57) ABSTRACT

Disclosed herein are metal-organic frameworks comprising at least two azolium rings. The azolium groups are used as a strategy for controlling catenation and morphology in metal-organic frameworks.

4 Claims, 7 Drawing Sheets

(56) References Cited

PUBLICATIONS

Crees, R. S. et al., "Synthesis of a Zinc(II) Imidazolium Dicarboxylate Ligand Metal-Organic Framework (MOF): a Potential Precursor to MOF-Tethered N-Heterocyclic Carbene Compounds", Inorg. Chem. 2010, 49, 1712-1719.

Herrmann, W. A., "N-Heterocyclic Carbenes: A New Concept in Organometallic Catalysis", Angew. Chem., Int. Ed. 2002, 41, 1290-1309.

Enders, D. et al., "Organocatalysis by N-Heterocyclic Carbenes", Chem. Rev. 2007, 107, 5606-5655.

Nair, V. et al., "Recent advances in carbon—carbon bond-forming reactions involving homoenolates generated by NHC catalysis" Chem. Soc. Rev. 2008, 37, 2691-2698.

Phillips, E. M. et al., "Discovering New Reactions with N-Heterocyclic Carbene Catalysis", Aldrichim. Acta 2009, 43, 55-66.

Phillips, E. M. et al., "N-Heterocyclic Carbene-Catalyzed Conjugate Additions of Alcohols", J. Am. Chem. Soc. 2010, 132, 13179-13181.

Cohen, D. T. et al., "NHC-Catalyzed/Titanium(IV)-Mediated Highly Diastereo- and Enantioselective Dimerization of Enals", Org. Lett. 2011, 13, 1068-1071.

Cohen, D. T. et al., "Lewis Acid Activated Synthesis of Highly Substituted Cyclopentanes by the N-Heterocyclic Carbene Catalyzed Addition of Homoenolate Equivalents to Unsaturated Ketoesters", Angew. Chem., Int. Ed. 2011, 50, 1678-1682.

Arduengo, A. J., "Looking for Stable Carbenes: The Difficulty in Starting Anew", Acc. Chem. Res. 1999, 32, 913-921.

Yadav, J. S. et al., "Microwave-accelerated conjugate addition of aldehydes to alpha,beta-unsaturated ketones", Tetrahedron Lett. 2003, 44, 8959-8962.

Barrett, A. G. M. et al., "ROMPgel-Supported Thiazolium Iodide: An Efficient Supported Organic Catalyst for Parallel Stetter Reactions" Org. Lett. 2004, 6, 3377-3380.

Tan, M. X. et al., "Hydrosilylation of Ketone and Imine over Poly-N-Heterocyclic Carbene Particles", Adv. Synth. Catal. 2009, 351, 1390-1394.

Rose, M. et al., "N-Heterocyclic carbene containing element organic frameworks as heterogeneous organocatalysts", Chem. Commun. 2011, 47, 4814-4816.

Jeong, N. et al., "Asymmetric catalytic reactions by NbO-type chiral metal-organic frameworks", Chem Sci 2011, 2, 877-882.

Lun, D. J. et al., "A General Thermolabile Protecting Group Strategy for Organocatalytic Metal-Organic Frameworks", J. Am. Chem. Soc. 2011, 133, 5806-5809.

Pangborn, A. B. et al., "Safe and Convenient Procedure for Solvent Purification", Organometallics 1996, 15, 1518-1520.

Zhu, L. et al., "An Improved Preparation of Arylboronates: Application in One-Pot Suzuki Biaryl Synthesis", J. Org. Chem. 2003, 68, 3729.

* cited by examiner

AZOLIUM METAL-ORGANIC FRAMEWORKS

This invention was made with government support under FA9550-07-1-0534 awarded by the Air Force Office of Scientific Research. The government has certain rights in the invention.

FIELD OF THE INVENTION

The present invention relates generally to a metal-organic framework comprising at least two azolium rings. The azolium groups are used as a strategy for controlling catenation and morphology in metal-organic frameworks.

BACKGROUND OF THE INVENTION

Metal-organic frameworks (MOFs) have emerged as a promising class of functional materials due to their microporosity, high internal surface area, and the ability to tune their structural and physical parameters (Ferey, G. *Chem. Soc. Rev.* 2008, 37, 191-214). These properties have led to the investigation of their application as materials for gas storage, gas separation, and catalysis (Murray, L. et al., *Chem. Soc. Rev.* 2009, 38, 1294-1314; Farha, O. K. et al., *Nat. Chem.* 2010, 2, 944-948; Furukawa, H. et al., *Science* 2010, 329, 424-428; Li, J. R. et al., *Chem. Soc. Rev.* 2009, 38, 1477-1504; Lee, J. et al., *Chem. Soc. Rev.* 2009, 38, 1450-1459). In contrast to the numerous reports regarding the application of MOFs toward these goals, there are far fewer reports on strategies for purifying these materials or for controlling their catenation, i.e. network interweaving or interpenetration (Farha, O. K. et al., *J. Am. Chem. Soc.* 2008, 130, 8598-8599). Nevertheless, a few strategies for regulating MOF catenation have been investigated, including "liquid-phase epitaxy", solvent or additive templating, solvent and/or concentration manipulation, and rational ligand design (Shekhah, O. et al., *J. Am. Chem. Soc.* 2007, 129, 15118-15119; Shekhah, O. et al., *Nat. Mater.* 2009, 8, 481-484; Ma, S. Q. et al., *J. Am. Chem. Soc.* 2007, 129, 1858-1859; Ma, L. Q. et al., *J. Am. Chem. Soc.* 2008, 130, 13834-13835; Wang, Q. et al., *Inorg. Chem.* 2009, 48, 287-295; Song, F. J. et al., *J. Am. Chem. Soc.* 2010, 132, 15390-15398; He, H. Y. et al., *Inorg. Chem.* 2010, 49, 7605-7607; Eddaoudi, M. et al., *Science* 2002, 295, 469-472; Zhang, J. J. et al., *J. Am. Chem. Soc.* 2009, 131, 17040-17041).

The most widely reported means of controlling catenation is by either solvent or additive-directed templating. For example, Zhou and co-workers have used oxalic acid as a templating agent and 1,10-phenanthroline as a sterically demanding group occupying coordination sites usually reserved for solvent. In a related report, Su and co-workers were able to demonstrate catenation control by guest inclusion in Cd(II)/Mn(II) 2D networks. Lin and co-workers have exploited the steric parameters of their solvent-dimethylformamide (DMF) vs diethylformamide (DEF) to achieve catenation control. A different approach was taken by Zhang et al. and by Eddaoudi et al., who employed low concentrations along with temperature parameters to modulate interpenetration. These strategies constitute important advances, but it remains to be seen if there is broad generality across different linkers, metals, and topologies.

Recently disclosed was an orthogonal approach to influence catenation by ligand design. Catenation can be influenced by modulating the size of substituents projected into the void space of certain MOF materials. This strategy has been successful across different strut types and even when incorporating large tetracarboxylate ligands (Farha, O. K. et al., *J. Am. Chem. Soc.* 2010, 132, 950-952; Farha, O. K. et al., *Inorg. Chem.* 2008, 47, 10223-10225). Also investigated was incorporating azolium salts, N-heterocyclic carbine (NHC) precursors, into metal-organic frameworks, a goal that has attracted considerable interest (Lee, J. Y. et al., *Inorg. Chem.* 2009, 48, 9971-9973; Fei, Z. F. et al., *Inorg. Chem.* 2005, 44, 5200-5202; Fei, Z. F. et al., *Inorg. Chem.* 2006, 45, 6331-6337; Chun, J. et al., *Inorg. Chem.* 2009, 48, 6353-6355; Han, L. J. et al., *Inorg. Chem.* 2009, 48, 786-788; Chun, J. et al., *Organometallics* 2010, 29, 1518-1521; Oisaki, K. et al., *J. Am. Chem. Soc.* 2010, 132, 9262-9264; Crees, R. S. et al., *Inorg. Chem.* 2010, 49, 1712-1719. While NHCs are versatile ligands for transition metals as well as organocatalysts in their own right, the potential application of coordination polymers containing these heterocyclic motifs is significant (Herrmann, W. A., *Angew. Chem., Int. Ed.* 2002, 41, 1290-1309; Nolan, S. P. *N-Heterocyclic Carbenes in Synthesis*; Wiley-VCH: Weinheim Chichester, 2006; Enders, D. et al., *Chem. Rev.* 2007, 107, 5606-5655. (b) Nair, V. et al., *Chem. Soc. Rev.* 2008, 37, 2691-2698; Phillips, E. M. et al., *Aldrichim. Acta* 2009, 43, 55-66; Phillips, E. M. et al., *J. Am. Chem. Soc.* 2010, 132, 13179-13181; Cohen, D. T. et al., *Org. Lett.* 2011, 13, 1068-1071; Cohen, D. T. et al., *Angew. Chem., Int. Ed.* 2011, 50, 1678-1682). Regarding their function as ligands, MOFs bearing NHCs could be functionalized with a metal of choice post-synthetically, yielding reusable heterogeneous transition metal catalysts with permanent microporosity. With respect to organocatalysis, NHCs immobilized in a MOF would not physically be capable of dimerization, a known nonproductive pathway under homogeneous conditions (Arduengo, A. J., *Acc. Chem. Res.* 1999, 32, 913-921). Heterogeneous materials for catalysis bearing azolium salts have been reported, but these materials lack defined, rigid structure and/or suffer from low porosity (Yadav, J. S. et al., *Tetrahedron Lett.* 2003, 44, 8959-8962; Barrett, A. G. M. et al., *Org. Lett.* 2004, 6, 3377-3380; Tan, M. X. et al., *Synth. Catal.* 2009, 351, 1390-1394; Rose, M. et al., *Chem. Commun.* 2011, 47, 4814-4816).

It is therefore desired to develop robust systems and increased turnover numbers with suitable azolium-MOF materials. It is further desired to (1) synthesize azolium salts capable of being incorporated into MOFs, (2) incorporate these unique, charged ligands into MOFs, and (3) utilize these metal-azolium frameworks as precursors for catalysts. Herein are reported new metal-azolium framework (MAF) materials using struts that vary the number, size, and electrostatic charge of the "side arm" type functional groups. This approach in turn has led to a new tactic to control catentation or morphology.

SUMMARY OF THE INVENTION

In light of the foregoing, it is an object of the present invention to provide a metal-organic framework (MAF) material with two or more azolium rings. This type of framework is a successful strategy for controlling catentation. As such, it is another object of the present invention to provide a method for reducing, eliminating or inhibiting cantenation in a metal-organic frameworks (MOF), the method comprising providing a biphenyl dicarboxylate derivative having at least two charged groups projecting into pores of the metal-organic framework, the at least two charged groups repulsing each other due to electrostatic van der Waals interactions and thereby reducing, eliminating or inhibiting cantentation of the MOF. The MOFs of the invention can be used as catalysts.

Accordingly, it will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Other objects, features, benefits and advantages of the present invention will be apparent from this summary and the following descriptions of certain embodiments, and will be readily apparent to those skilled in the art. Such objects, features, benefits and advantages will be apparent from the above as taken into conjunction with the accompanying examples, data, and all reasonable inferences to be drawn therefrom.

BRIEF DESCRIPTION OF THE DRAWINGS

FIG. 2 Single crystal X-ray structures of A) MOF I down the a, b and c axis; and B) MOF II down the a, b and c axis.

DETAILED DESCRIPTION OF THE INVENTION

Accordingly, the present invention includes a metal-organic framework comprising at least two heterocyclic quaternary salts, such as azolium salts. Illustrating certain non-limiting aspects and embodiments of the invention, the azolium salts of the present invention can be imidazolium salts.

Figure 1:
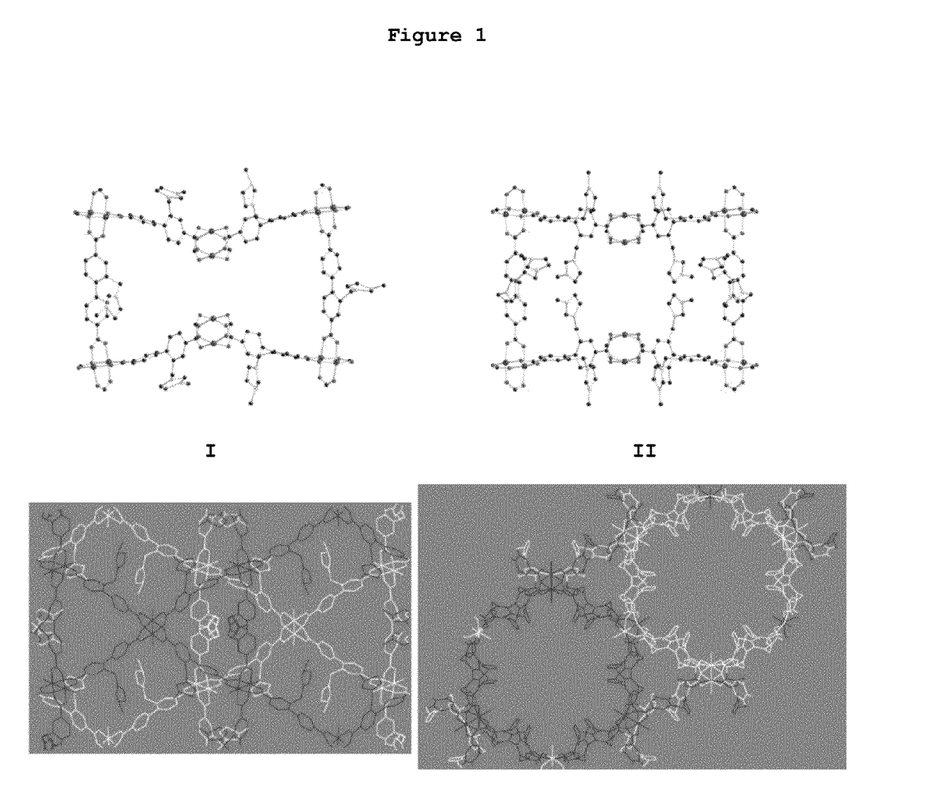
FIG. 1 Single crystal X-ray structures of MOF I and MOF II.
Figure 2A:
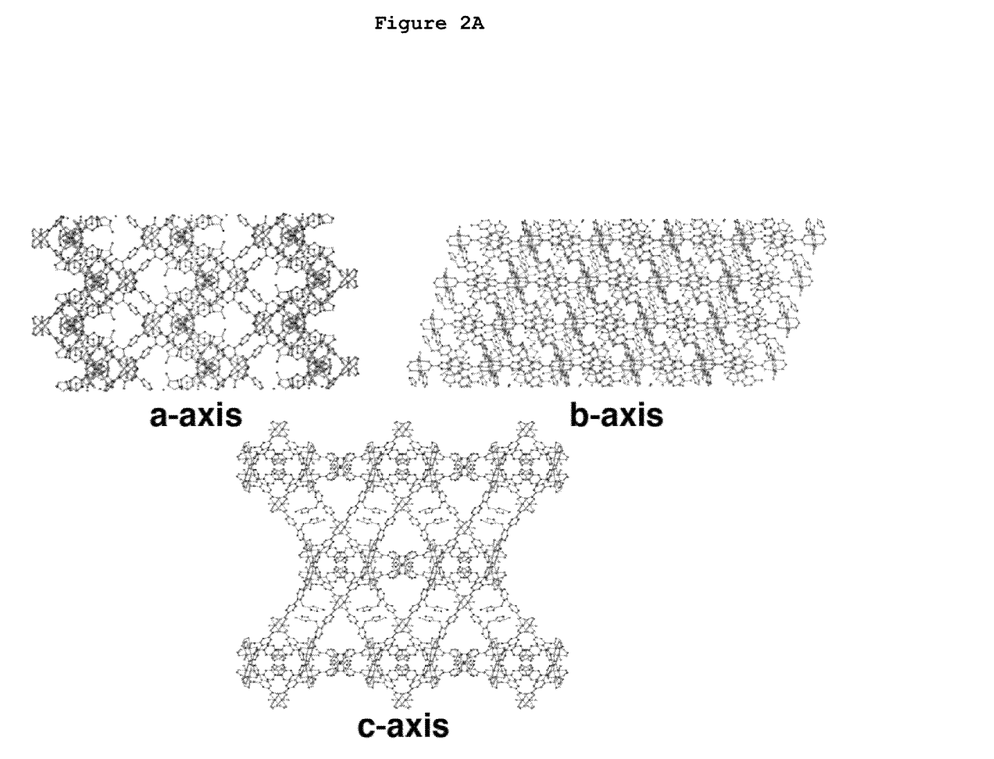

In a preferred embodiment, two biphenyl dicarboxylate (bpdc) based linkers with appended methyl imidazolium salts are prepared according to Scheme 1. Referring to Scheme 1, 3 is combined with $Cu(NO_3)_2 \cdot 3H_2O$ in a 1:1 DMF/EtOH (DMF=dimethylformamide; EtOH=ethanol) mixture at 110° C., deep blue crystals with a framework formula of $Cu_2(3)_2 \cdot 2(DMF_x/EtOH_{1-x})$ (I) are obtained after sitting overnight. Single crystal X-ray diffraction reveals these crystals to contain two independent sets of 2D sheets, each containing $Cu_2(CO_2)_4$ paddlewheel SBUs bridged by 3 (FIG. 1), yielding a subunit similar to the one reported by Jeong and co-workers (see Jeong, N. et al., *Chem Sci* 2011, 2, 877-882, incorporated herein by reference). Referring to FIG. 1, the left portion depicts a subunit of I and view down the c-axis of the unit cell, with each of the two independent networks shown in a different shade. FIG. 2A shows a view of II down the a, b and c axis.

Scheme 1

X = H (1)
X = Me (2)

X = H
X = $CH_2Br$

X = H (3)
X = imidazolium bromide (4)

Figure 2B:
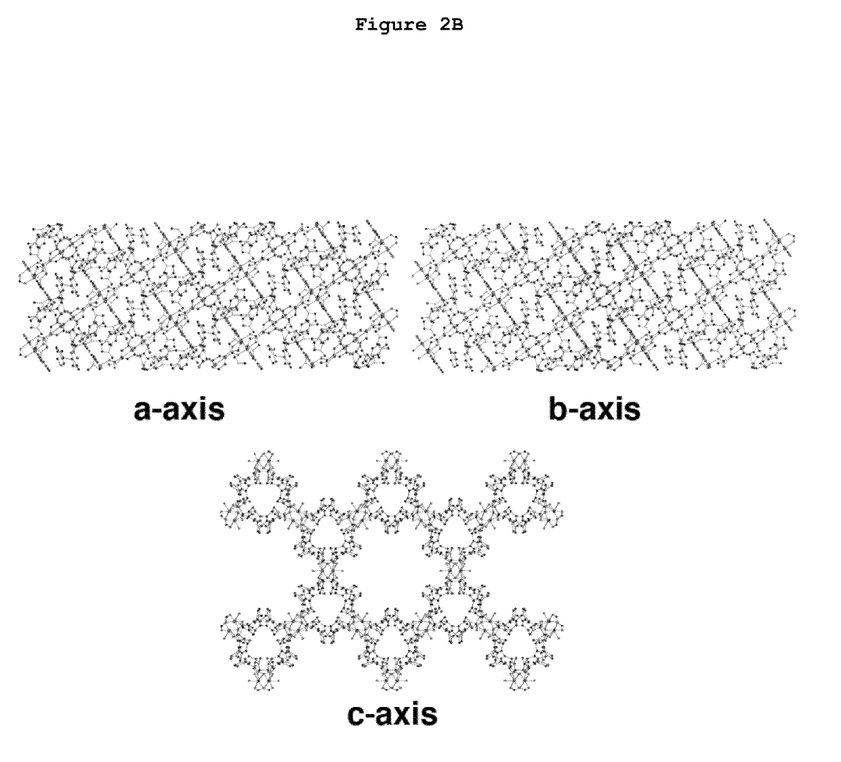

Next, and again referring to Scheme 1, combining 4 with $Cu(NO_3)_2 \cdot 3H_2O$ under identical reaction conditions as used to make I yielded deep blue crystals with a framework formula of $Cu_2(4) \cdot 2(DMF_x/EtOH_{1-x})$ (II). Single crystal X-ray diffraction reveals II to still contain two independent sets of 2D sheets and the same repeating unit as I. However, II possesses a different morphology than I and contains much larger channels (ca. 13 Å across). Referring to FIG. 1, the right portion of the diagram depicts a subunit of II and view down the c-axis of the unit cell, with each of the two independent networks shown in a different shade. FIG. 2B shows a view of II down the a, b and c axis.

Figure 3:
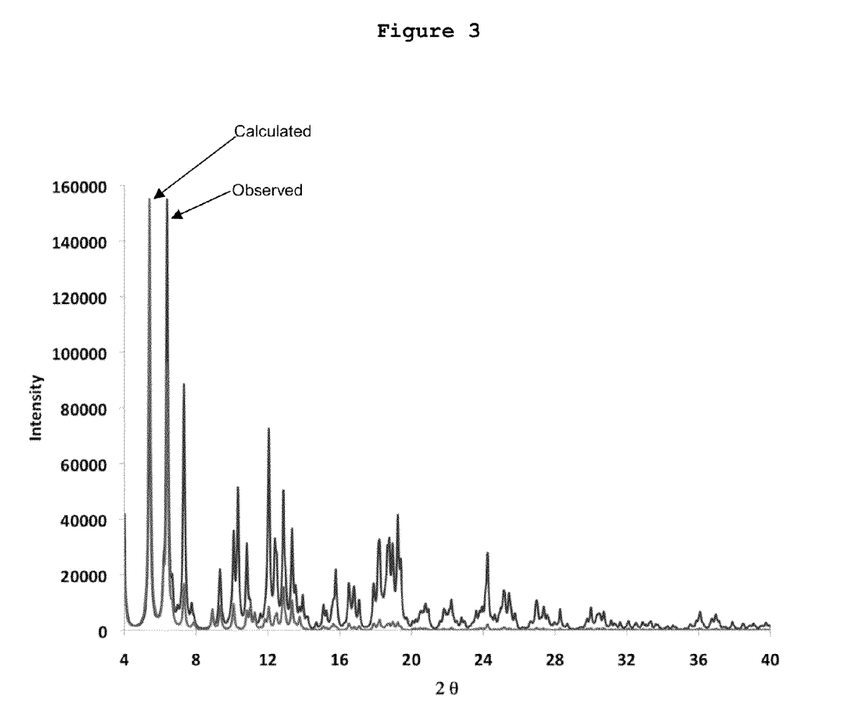
FIG. 3 Powder X-ray diffraction of MOF I.
Figure 4:
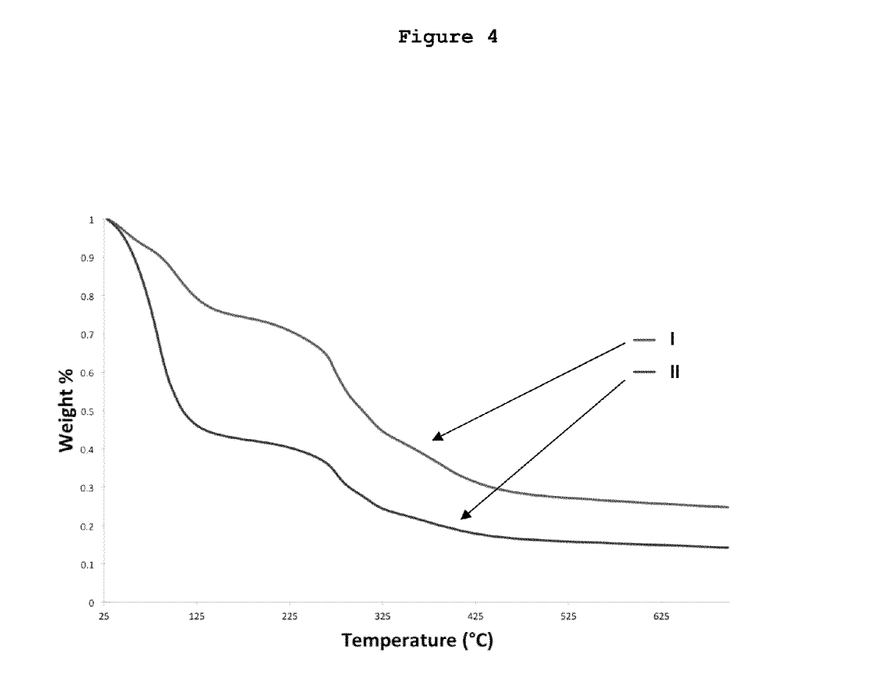
FIG. 4 Thermogravimetric analysis of MOF I and MOF II.

Powder X-ray diffraction (PXRD) likewise shows these materials to be distinct from one another (see FIGS. 3A and 3B). Apart from the crystallographic evidence, the different morphology is apparent in thermogravimetric analysis (TGA) traces for I and II (FIG. 4). As anticipated, II exhibits greater mass loss (solvent DMF and EtOH molecules) than I between 25 and 275° C. I loses approximately 25% of its weight before decomposition, whereas II loses roughly 60%.

Figure 5:
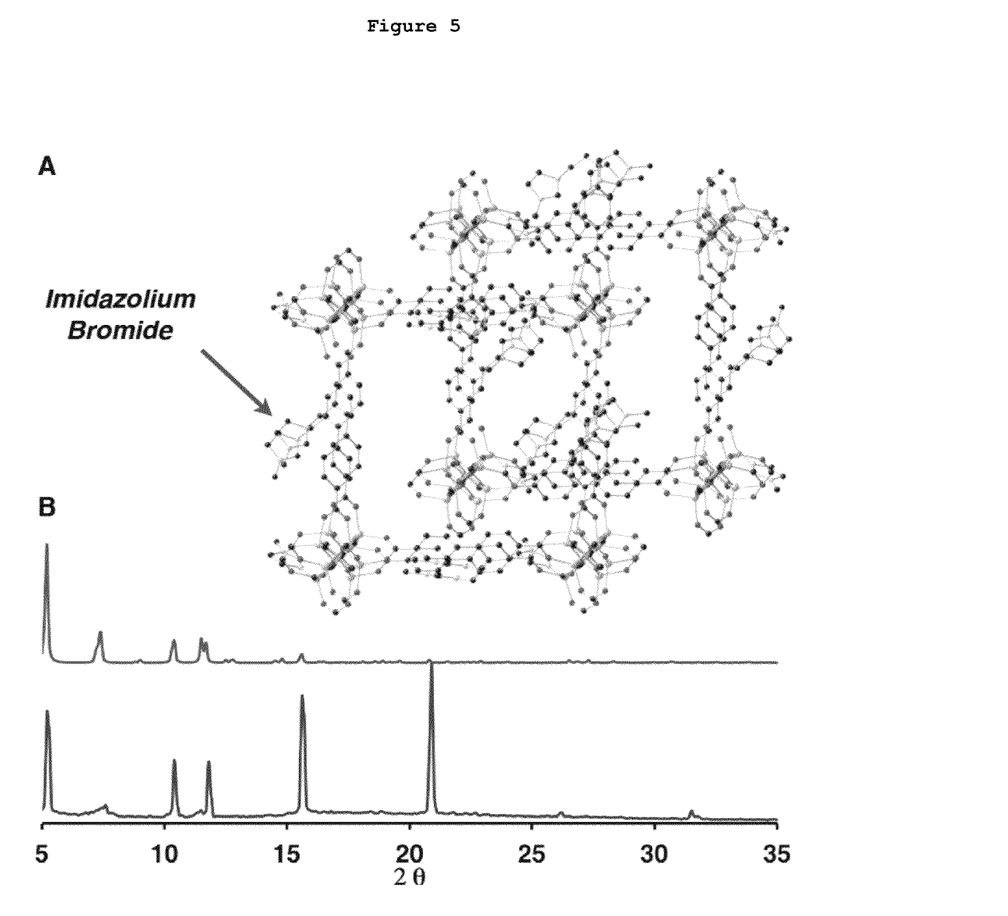
FIG. 5 A) Single crystal X-ray structure of catenated repeating units of III; and B) Powder X-ray diffraction of III.

In another aspect of the invention, zinc MAFs are also synthesized. To this end, it was hypothesized that when combined with $Zn(NO_3)_2 \cdot 6H_2O$, strut 3 would yield cubic networks with $Zn_4O$ nodes, similar to the noncatenated material IRMOF-10 (see Eddaoudi et al., *Science* 2002, 295, 469-472, incorporated herein by reference), since 3 is similar to bpdc but possesses more steric bulk. The combination of 3 with $Zn(NO_3)_2 \cdot 6H_2O$ in DMF and heated at 90° C. for 2 days gave colorless, block crystals with a framework formula of $Zn_4O$ $(3)_3$ (III). Single-crystal X-ray analysis reveals the crystals to comprise a catenated pair of networks, i.e. analogous to IRMOF-9 instead of IRMOF-10 (FIG. 5). In hopes of producing an IRMOF-10 derivative, 4 is combined with $Zn(NO_3)_2 \cdot 6H_2O$ in DMF and heated at 90° C. for 2 days. Once again, colorless block crystals (IV) are obtained. Interestingly, these crystals do not furnish a satisfactory single crystal diffraction pattern.

Figure 6:
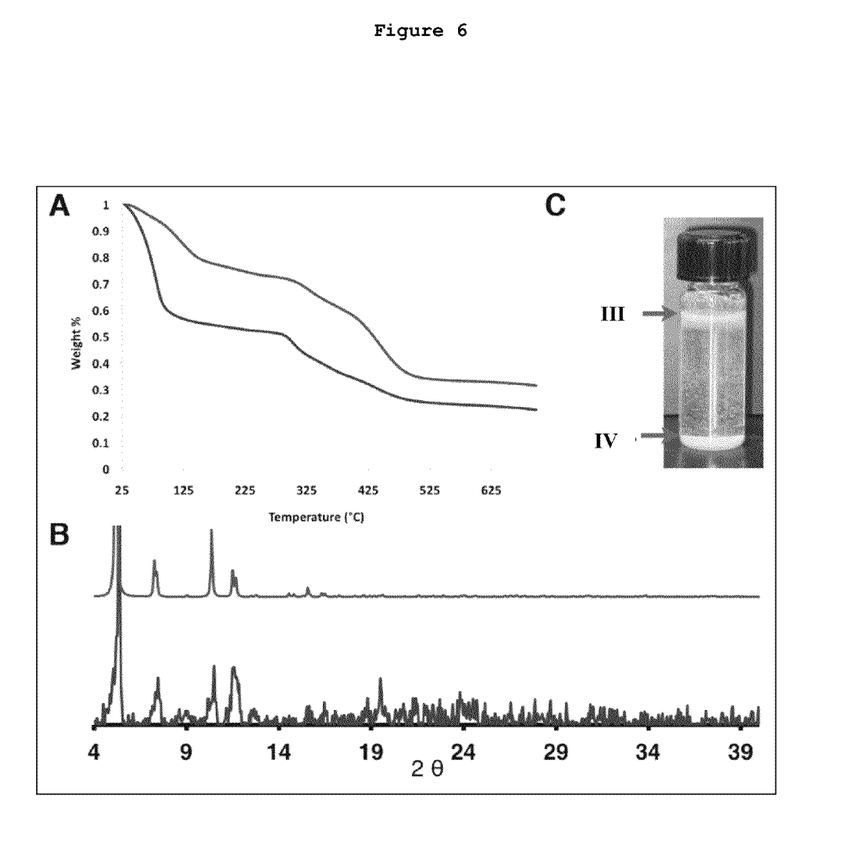
FIG. 6 A) Thermogravimetric analysis showing traces of III and IV; B) Powder X-ray diffraction of IV; and C) density separation experiment.

Consequently, other techniques are used to characterize IV, seeking to determine if this material is in fact an IRMOF-10 analogue. PXRD reveals IV to be distinct from IV (FIG. 6B), and the powder pattern for IV closely resembles a predicted powder pattern generated from a computational model that removed one of the interpenetrating networks in III. This comparison supports the assessment that IV is an IRMOF-10 analogue. In addition to the PXRD data, a density separation experiment provides further support for IV possessing an uncatenated framework, since it possesses a lower density respective to III (see Farha, O. K. et al., *J. Am. Chem. Soc.* 2008, 130, 8598-8599, incorporated herein by reference). FIG. 6C shows that III sinks to the bottom whereas IV floats with the appropriate solvent composition (0.8:1 v:v DMSO/$CH_2BrCl$; DMSO=dimethyl sulfoxide; $CH_2BrCl$=bromochloromethane), even though the strut is heavier. TGA measurements result in a similar conclusion. As anticipated, IV experiences greater solvent loss than III (45% of its weight as opposed to 25% for III). The combined experiments of TGA (FIG. 6A), comparison of simulated and predicted PXRD (FIG. 6B), and density separation (FIG. 6C) support the conclusion that IV is indeed the non-catenated, double azolium framework analogous to IRMOF-10.

The primary factor contributing to the observed inhibition of catenation or change in morphology is the additional azolium "side arm" of strut 4 (vs 3) which projects into the pore of IV. This structural element (steric and charged substituent directing into the pore) has been implicated in the generation of other IRMOF-10-type derivatives in a related system (Lun, D. J. et al., *J. Am. Chem. Soc.* 2011, 133, 5806-5809, incorporated herein by reference). Although a few examples of influencing catenation by adding steric elements have recently appeared in the MOF literature, it is believed that each case is system-specific, i.e. two or more charged groups repulsing each other due to electrostatic van der Waals interactions. Furthermore, while this strategy results in higher porosity due to the removal of an interpenetrated network, the additional steric elements in the existing framework may result in pores that are partially or fully blocked. Another influence on catenation is presumably the unusual electrostatic environment created by increasing the number of imidazolium groups arrayed within the pore of MOF IV. This unusual property contributes to unusually high hydrogen absorption energies. To date, all bases (various alkoxides and amines) to which IV has been exposed, with the aim of creating catalytically active N-heterocyclic carbine (NHCs), have been found to promote framework degradation.

The MOFs disclosed herein can be considered in the context of coordination of an inorganic metal center block component with one or more organic linker/ligand block components comprising two or more terminal heterocyclic quaternary salts, such as azolium salts, and preferably imidazolium salts. Specific examples of metals contemplated include, but are not limited to, any oxidation state of magnesium, calcium, strontium, barium, radium, aluminum, gallium, indium, thallium, silicon, germanium, tin, lead, arsenic, antimony, scandium, titanium, vanadium, chromium, manganese, iron, cobalt, nickel, copper, zinc, yttrium, zirconium, niobium, molybdenum, technetium, rubidium, rhodium, palladium, silver, cadmium, hafnium, tantalum, tungsten, rhenium, osmium, iridium, platinum, gold, mercury, lanthanum, cerium, praseodymium, neodymium, promethium, samarium, europium, gadolinium, terbium, dysprosium, holmium, erbium, thulium, and ytterbium. Metal components that can coordinate to such ligands comprise metal ions such as but not limited to Mg2+, Ca2+, Sr2+, Ba2+, Sc3+, Y3+, Ti4+, Zr4+, Hf4+, V4+, V3+, V2+, Nb3+, Ta3+, Cr3+, Mo3+, W3+, Mn3+, Mn2+, Re3+, Re2+, Fe3+, Fe2+, Ru3+, Ru2+, Os3+, Os2+, Co3+, C2+, Rh2+, Rh+, Ir2+, Ir+, Ni2+, Ni+, Pd2+, Pd+, Pt2+, Pt+, Cu2+, Cu+, Ag+, Au+, Zn2+, Cd2+, Hg2+, Al3+, Ga3+, In3+, Tl3+, Si4+, Si2+, Ge4+, Ge2+, Sn4+, Sn2+, Pb4+, Pb2+, As5+, As3+, As+, Sb5+, Sb3+, Sb+, and Bi5+, Bi3+, and Bi+. Such metal ions are available through corresponding metal salts, in conjunction with any acceptable counter ion(s), such as but not limited to nitrate. In certain non-limiting embodiments, such metals can be transition metals, such as any oxidation state of vanadium, copper, zinc and zirconium. Specific metals and oxidation states contemplated for use in the MOFs disclosed herein include, but are not limited to, Zr4+, V4+, V3+, Cu2+, Cu+, and Zn2+. Without limitation, as can relate to various MOFs illustrated herein, metal centers associated with inorganic block components can include $Cu_2$, $Zn_4O$, $Zn_2$, $V_2O_3$, and $Zr_6O_6$.

As provided for herein, the MOFs can be polymeric crystalline structures, which are polymers of inorganic metal center block components coordinated to one or more organic linker/ligand block components. The materials produced herein can be "crystalline," which refers to the ordered definite crystalline structure, such a material which is unique and thus identifiable by a characteristic X-ray diffraction pattern.

In some cases, the MOFs disclosed herein are substantially free of solvents. As used herein "substantially free" means that solvents are present in the MOF at levels less than 1 wt % by weight of the MOF, and preferably from 0 wt % to about 0.5 wt % by weight of the MOF. The solvent can be removed from the MOF by exposing the MOF to elevated temperatures under reduced pressure, or by soaking the MOF in a low boiling solvent to exchange the coordinated solvent for the low boiling solvent, then exposing the MOF to reduced pressure. The amount of solvent in the MOF can be determined by elemental analysis or other known analytical techniques.

EXAMPLES

General

All reactions are carried out under a nitrogen atmosphere in flame-dried glassware with magnetic stirring unless otherwise stated. All reagents are purchased from Aldrich unless otherwise stated. $CH_3CN$ (acetonitrile) is purified by passage through a bed of activated alumina (see Pangborn, A. B. et al., *Organometal.* 1996, 15, 1518-1520, incorporated herein by reference). Reagents are purified prior to use unless otherwise stated following the guidelines of Perrin and Armarego (see Perrin, D. D. and Armarego, W. L., *Purification of Laboratory Chemicals;* 3rd Ed., Pergamon Press, Oxford. 1988, incorporated herein by reference). Analytical thin layer chromatography is performed on EM Reagent 0.25 mm silica gel 60° F. plates. Visualization is accomplished with UV light. $^1$H-NMR spectra are recorded on a Bruker AVANCE III 500 (500 MHz) spectrometer and are reported in ppm using solvent as an internal standard ($CDCl_3$ at 7.26 ppm, DMSO-$d_6$ at 2.50 ppm, and $D_2SO_4$ at 10.5 ppm). Data are reported as (ap=apparent, s=singlet, d=doublet, t=triplet, q=quartet, m=multiplet, b=broad) coupling constant(s) in Hz; integration. Proton-decoupled $^{13}$C-NMR spectra are recorded on a Bruker AVANCE III 500 (125 MHz) spectrometer and are reported in ppm using solvent as an internal standard ($CDCl_3$ at 77.16 ppm and DMSO-$d_6$ at 39.52 ppm). Mass spectra data is obtained on an Agilent 1100 Series LC/MSD. FTIR spectra data is obtained on a Bruker Tensor 37 FTIR. Compounds are named herein using ChemDraw Ultra 12.0 or 13.0.

Example 1

Dimethyl 2-methylbiphenyl-4,4'-dicarboxylate (1)

This compound is prepared according to a preexisting literature procedure, i.e. Zhu, L. et al., *J. Org. Chem.* 2003, 68, 3729, incorporated herein by reference).

Example 2

Dimethyl 2,2'-dimethylbiphenyl-4,4'-dicarboxylate (2)

This compound is prepared using a modified literature procedure as described in Zhu et al. The reaction is run on a 7.8 mmol scale according to the literature procedure. Methyl 3-methyl-4-bromobenzoate is used in both steps of the reaction. After workup the resulting solid is purified by flash column chromatography ($SiO_2$, 10% EtOAc/Hexane) yielding 2 (1.94 g, 84%) as white crystalline solid. Analytical data for 2: IR (ATR) 2953, 1713, 1453, 1285, 1253, 1200, 1113, 1005, 773 cm$^{-1}$; $^1$H NMR (500 MHz, $CDCl_3$) δ 7.97 (s, 2H), 7.91 (d, J=9.2 Hz, 2H), 7.15 (d, J=15 Hz, 2H) 3.94 (s, 6H), 2.07 (s, 6H); $^{13}$C (125 MHz, $CDCl_3$) δ 167.2, 145.6, 136, 131.3, 129.5, 129.1, 127.1, 52.3, 19.8; HRMS (CI): Exact mass calcd for $C_{14}H_{18}O_4$ [M+1]$^+$, 299.12. Found: 299.1.

Example 3

3-((4,4'-dicarboxybiphenyl-2-yl)methyl)-1-methyl-1H-imidazol-3-ium bromide (3)

To a 100 ml round bottom flask containing a stir bar is added 1 (2.54 g, 8.96 mmol), N-bromo succinimide (1.83 g, 10.3 mmol), AIBN (0.147 g, 0.896 mmol) and $CCl_4$ (45 ml). The flask is fitted with a reflux condenser and refluxed for 3 hours or until thin layer chromatography (TLC) (30% EtOAc/Hex) shows full conversion. The contents of the flask are directly filtered into a 100 ml round bottom flask to remove the succinimide and the filtrate is concentrated under reduced pressure to yield a pale yellow semi-solid. This solid is dried under high vacuum overnight. A stir bar is added to the flask containing the crude brominated compound and $CH_3CN$ (45 ml) and 1-methyl imidazole (1.56 ml, 19.7 mmol) are added. The flask is fitted with a reflux condenser and heated at 80° C. for 2 hours. After cooling to room temperature, the reaction mixture is transferred to a 200 ml round bottom flask and concentrated under reduced pressure to yield a brown oil. This oil is dried under high vacuum yielding the crude imidazolium bromide as a tan foam. To the flask containing the crude imidazolium bromide is added a stir bar and the foam is dissolved in 90 ml of a 3:1 MeOH:$H_2O$ mixture. LiOH (3.67 g, 89.6 mmol) is added in one portion and the reaction stirred for three hours at 23° C. After three hours, the reaction mixture is acidified to pH 1 with HBr (conc., 48% w/w) and the MeOH is removed under reduced pressure. After ~50 ml of solvent is removed a white precipitate fell out of solution. This precipitate is filtered, washed with water, and dried under high vacuum yielding 3 (2.175 g, 62%) as an off-white solid. Analytical data for 3: IR (ATR) 3356, 2972, 1713, 1648, 1605, 1384, 1290, 1238, 1161, 1100, 953, 815 cm$^{-1}$; $^1$H NMR (500 MHz, DMSO-$d_6$) δ 8.76 (s, 1H) 8.06 (d, J=9.4 Hz, 1H) 8.01 (d, J=8.3 Hz, 2H) 7.97 (s, 1H) 7.61 (s, 1H) 7.46 (d, J=8.9 Hz, 1H) 7.42 (d, J=8.2 Hz, 2H) 7.40 (s, 1H) 5.46 (s, 2H) 3.74 (s, 3H); $^{13}$C (125 MHz, DMSO-$d_6$) δ 167, 166.7, 144.8, 142.8, 136.9, 132.3, 131.1, 130.8, 130.5, 130.3, 129.8, 129.6, 128.8, 123.8, 122.5, 50.2, 35.8; HRMS (CI): Exact mass calcd for $C_{19}H_{17}O_4N_2$ [M]$^+$, 337.12. Found: 337.1.

Example 4

3,3'-(4,4'-dicarboxybiphenyl-2,2'-diyl)bis(methylene) bis(1-methyl-1H-imidazol-3-ium) bromide (4)

To a 50 ml round bottom flask containing a stir bar is added 2 (1.21 g, 4.06 mmol), N-bromo succinimide (1.59 g, 8.94 mmol), AIBN (0.066 g, 0.406 mmol) and $CCl_4$ (20 ml). The flask is fitted with a reflux condenser and refluxed for 3 hours or until TLC (30% EtOAc/Hex) shows full conversion. The contents of the flask are directly filtered into a 50 ml round bottom flask to remove the succinimide and the filtrate is concentrated under reduced pressure to yield a pale yellow oil. This oil is dried under high vacuum overnight. A stir bar is added to the flask containing the crude brominated compound and $CH_3CN$ (20 ml) and 1-methyl imidazole (0.73 ml, 8.94 mmol) are added. The flask is fitted with a reflux condenser and heated at 80° C. for 2 hours. After cooling to room temperature, the reaction mixture is transferred to a 100 ml round bottom flask and concentrated under reduced pressure to yield a brown oil. This oil is dried under high vacuum yielding the crude imidazolium bromide as a tan foam. To the flask containing the crude imidazolium bromide is added a stir bar and the foam is dissolved in 40 ml of a 1:1 THF:$H_2O$ mixture. LiOH (1.66 g, 40.6 mmol) is added in one portion and the reaction stirred for three hours at 23° C. After three hours, the reaction mixture is acidified to pH 1 with HBr (conc., 48% w/w) and the THF is removed under reduced pressure. After ~20 ml of solvent is removed the contents of the flask are filtered to remove any solid and the filtrate is left to crystallize. After ~24 hours white needle crystals began to fall out of solution. In subsequent reactions the filtrate is seeded with product. The crystals are filtered, washed with water, and dried under high vacuum yielding 4 (1.076 g, 45%) as a white crystalline solid. Analytical data for 4: IR (ATR) 3383, 2972, 1710, 1379, 1284, 1261, 1161, 952 cm$^{-1}$; $^1$H NMR (500 MHz, DMSO-$d_6$) δ8.73 (s, 2H), 8.01 (s, 2H), 7.96 (d, J=9.2 Hz, 2H), 7.66 (s, 2H), 7.43 (s, 2H), 7.18 (d, J=8.9 Hz) 5.24 (dd, J=104 Hz), 3.77 (s, 3H); $^{13}$C (125 MHz, DMSO-$d_6$) δ 166.6, 142.2, 136.8, 132.5, 131.4, 130.7, 130, 129.8, 123.8, 122.5, 50.2, 35.9; HRMS (CI): Exact mass calcd for $C_{24}H_{24}O_4N_4$ [M/2]$^+$, 216.09. Found: 216.1.

Example 5

Preparation of MOF I and MOF II—A single crystal of I is synthesized via solvothermal reaction of $Cu(NO_3).3H_2O$ (0.726 mmol, 0.175 g) and 3 (0.242 mmol, 0.1 g) in 10 ml of a 1:1 DMF:EtOH solution. The reagents and solvent are added to a 20 ml scintillation vial and sonicated until the solution is homogeneous. This vial is placed in an oven set to 110° C. After 3 hours deep teal crystals are visible. After heating overnight, the solvent is replaced with fresh DMF: EtOH which has been warmed to 110° C. and the vial is allowed to cool to room temperature. Crystals are stored at room temperature under the 1:1 DMF:EtOH solvent mixture. II is prepared in an analogous manner, except using 0.168 mmol (0.1 g) of 4 (instead of 3) and 0.5 mmol (0.122 g) of $Cu(NO_3)_2 \cdot 3H_2O$.

Example 6

Preparation of MOF III and MOF IV—A single crystal of III is synthesized via solvothermal reaction of $Zn(NO_3)_2 \cdot 6H_2O$ (0.3 mmol, 0.089 g) and 3 (0.1 mmol, 0.041 g) in 7 ml of DMF. The reagents and solvent are added to a 20 ml scintillation vial and sonicated until the solution is homogeneous. This vial is placed in an oven set to 90° C. After heating overnight, small block crystals are observed. After 36 hours of heating the solvent is replaced with fresh DMF which has been warmed to 90° C. and the vial is allowed to cool to room temperature. Crystals are stored at room temperature under DMF. IV is prepared in an analogous manner, except using 0.1 mmol (0.059 g) of 4.

Example 7

Characterization of MOFs—Single crystals of I, II, and III are mounted in oil on glass fibers and placed in a nitrogen cold stream at 100K of a Bruker AXS APEX2 diffractometer equipped with a CCD detector and graphite monocrhomated $CuK\alpha$ (I, III) or $MoK\alpha$ (II) radiation. All data is corrected for absorption via SADABS. Structures are solved and refined using the SHELXTL suite of software. The program SQUEEZE (Platon) is used to remove electronic contributions from solvent molecules for each structure.

IR spectra of I-IV are collected on a Bruker Tensor 37 FTIR with an ATR attachment. IR data for I (ATR) 3480, 1666, 1393, 1107, 780, 684, 667 $cm^{-1}$. IR data for II (ATR) 3444, 1668, 1391, 1164, 1107, 782, 682, 667 $cm^{-1}$. IR data for III (ATR) 1668, 1616, 1339, 1165, 783, 679, 667 $cm^{-1}$. IR data for IV (ATR) 1668, 1606, 1390, 1103, 781, 682, 665 $cm^{-1}$.

Powder patterns for I and II are collected on Bruker AXS APEX2 diffractometer equipped with a CCD detector and a $CuK\alpha$ IµS microfocus source with MX optics. Samples are mounted in glass capillaries with a small amount of mother-liquor. Data are collected with an area detector as rotation frames over 180° in φ at 2θ values of 12°, 24°, and 36° and exposed for 10 minutes for each frame. At a distance of 150 mm, the detector area covers 24° in 2θ. Overlapping sections of data are matched and the resulting pattern integrated using the Bruker APEX2 Phase ID program. Powder pattern data are treated for amorphous background scatter (EVA 16, Copyright Bruker-AXS 1996-2010).

PXRD patterns for III and IV are collected using a Rigaku XDS 2000 diffractometer using $CuK\alpha$ radiation (λ=1.5418 Å). Predicted PXRD spectra are generated using Mercury v. 2.4 for Mac OsX. Samples are mounted on quartz sample holders as a slurry of ground MOF and DMF.

TGA is recorded on a Mettler Toledo TGA/SDTA851e interfaced with a PC using Star software. The heating range is from 25° C. to 700° C. The heating rate is 10° C./min under a nitrogen atmosphere. All samples are filtered directly from DMF or 1:1 DMF:EtOH solutions before the experiment.

The density separation experiment preformed on III and IV is carried out in the method reported by Farha et al. (Farha, O. K. et al., *J. Am. Chem. Soc.* 2008, 130, 8598, incorporated herein by reference). Material that is shown to be III via PXRD sinks to the bottom of a 1 dram vial containing a 4:5 mixture of $DMSO:CH_2BrCl$. Material that is shown to be IV via PXRD rises to the top of a 1 dram vial containing a 4:5 mixture of $DMSO:CH_2BrCl$. When a mixture of III and IV is added to a 1 dram vial containing a 4:5 mixture of $DMSO:CH_2BrCl$, the materials separate in ~30 seconds. The predicted PXRD of IV is generated by a computational program developed by Chris Wilmer et al.

In conclusion, the ability to manipulate the morphology of distinct Cu-paddlewheel and cubic systems using new azolium-based ligands: 2D copper paddlewheel sheets and isoreticular networks similar to IRMOF-9 and -10, is demonstrated. Catenation control is observed by a combination of single crystal X-ray diffraction, PXRD, density separation, and TGA experiments. The incorporation of different numbers of charged groups such as azolium salts into porous materials impact the level of catenation or morphology.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter described herein without departing from its scope. While the dimensions and types of materials described herein are intended to define the parameters of one or more embodiments of the inventive subject matter, they are by no means limiting and are example embodiments. Many other embodiments will be apparent to one of ordinary skill in the art upon reviewing the above description. The scope of the subject matter described herein should, therefore, be determined with reference to the appended clauses, along with the full scope of equivalents to which such clauses are entitled. In the appended clauses, the terms "including" and "in which" are used as the plain-English equivalents of the respective terms "comprising" and "wherein." Moreover, in the following clauses, the terms "first," "second," and "third," etc. are used merely as labels, and are not intended to impose numerical requirements on their objects.

This written description uses examples to disclose several embodiments of the inventive subject matter and also to enable any person of ordinary skill in the art to practice the embodiments disclosed herein, including making and using any devices or systems and performing any incorporated methods. The patentable scope of the subject matter is defined by the clauses, and may include other examples that occur to one of ordinary skill in the art. Such other examples are intended to be within the scope of the clauses if they have structural elements that do not differ from the literal language of the clauses, or if they include equivalent structural elements with insubstantial differences from the literal languages of the clauses.

The foregoing description of certain embodiments of the disclosed subject matter will be better understood when read in conjunction with the appended drawings. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of addi- tional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described systems and methods, without departing from the spirit and scope of the subject matter herein involved, it is intended that all of the subject matter of the above description or shown in the accompanying drawings shall be interpreted merely as examples illustrating the inventive concepts herein and shall not be construed as limiting the disclosed subject matter.

The disclosures of all articles and references, including patents, are incorporated herein by reference. The invention and the manner and process of making and using it are now described in such full, clear, concise and exact terms as to enable any person skilled in the art to which it pertains, to make and use the same. All references cited in this specification are incorporated herein by reference.

What is claimed is:

1. An azolium-based metal organic framework comprising a structure of a metal ion selected from the group consisting of $2(Cu^+)$ and $Zn_4O$, and a biphenyl dicarboxylate derivative of the formula wherein X is selected from H (3) and (4), and wherein
the structure is characterized in that the biphenyl dicarboxylate derivative is coordinated to the metal ion through the dicarboxylate portion of the biphenyl dicarboxylate derivative.

2. An azolium-based metal organic framework according to claim 1 wherein X is 3. An azolium-based metal organic framework according to claim 1 wherein the metal ion is $2(Cu^+)$.

4. An azolium-based metal organic framework according to claim 2 wherein the structure has a formula selected from the group consisting of $Cu_2(4).2(DMF_y/EtOH_{1-y})$ and $Zn_4O(4)_3$, wherein DMF and EtOH are solvent molecules dimethylformamide and ethanol, respectively, and y is the number of DMF solvent molecules.

* * * * *